United States Patent
Zama et al.

(10) Patent No.: US 7,420,668 B2
(45) Date of Patent: Sep. 2, 2008

(54) WAFER SURFACE INSPECTION APPARATUS AND WAFER SURFACE INSPECTION METHOD

(75) Inventors: Kazuhiro Zama, Mito (JP); Masayuki Hachiya, Tokorozawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/501,922

(22) Filed: Aug. 10, 2006

(65) Prior Publication Data

US 2007/0182957 A1    Aug. 9, 2007

(30) Foreign Application Priority Data

Aug. 11, 2005    (JP)    ............................. 2005-233314

(51) Int. Cl.
*G01N 21/88* (2006.01)
*H01J 37/26* (2006.01)
*B08B 7/04* (2006.01)

(52) U.S. Cl. .................. 356/237.2; 314/18; 250/307

(58) Field of Classification Search ... 356/237.1–237.6; 219/121.84, 121.85; 134/1.3, 2, 18, 109; 382/145, 149, 153; 250/307, 310

See application file for complete search history.

(56) References Cited

U.S. PATENT DOCUMENTS

| | | | | |
|---|---|---|---|---|
| 5,865,901 A | * | 2/1999 | Yin et al. | 134/2 |
| 5,958,268 A | * | 9/1999 | Engelsberg et al. | 219/121.84 |
| 6,005,660 A | * | 12/1999 | Yoshida et al. | 356/237.3 |
| 6,356,653 B2 | * | 3/2002 | Brigante et al. | 382/145 |
| 6,566,169 B1 | * | 5/2003 | Uziel et al. | 438/115 |
| 6,799,584 B2 | * | 10/2004 | Yogev et al. | 134/1.3 |
| 6,844,458 B2 | * | 1/2005 | Copeland et al. | 554/212 |
| 7,159,599 B2 | * | 1/2007 | Verhaverbeke et al. | 134/109 |
| 2003/0029479 A1 | * | 2/2003 | Asano | 134/18 |

FOREIGN PATENT DOCUMENTS

JP    55-102233 A    8/1980

* cited by examiner

*Primary Examiner*—Sang Nguyen
(74) *Attorney, Agent, or Firm*—McDermott Will & Emery LLP

(57) ABSTRACT

A wafer surface inspection method and apparatus of high sensitivity, and free from performance degradation in terms of cleanliness, coordinate repeatability of foreign particles and the like. Gas for cooling is sprayed onto a laser irradiation position on the wafer surface to prevent an increase in temperature of the foreign particles and to suppress break-down of the foreign particles.

6 Claims, 6 Drawing Sheets

WAFER SURFACE INSPECTION APPARATUS AND WAFER SURFACE INSPECTION METHOD

BACKGROUND OF THE INVENTION

The present invention relates to a surface inspection apparatus and a surface inspection method of a subject to be inspected, and relates for example to a wafer surface inspection apparatus and a wafer surface inspection method for inspecting for foreign particles or foreign matter, defects and the like on a semiconductor wafer surface in a manufacturing process of a semiconductor device.

In a manufacturing process of a semiconductor device, a circuit is formed by transferring a pattern onto a bare wafer and etching the same. In the manufacturing processes of various semiconductor devices during which circuits are formed, foreign particles adherent to the wafer surface, defects and the like become major factors causing a decrease in yield. The foreign particles adherent to the wafer surface and the defects are managed in each manufacturing process, and a wafer surface inspection apparatus detects the foreign particles adherent to the bare wafer surface, the defects present on the wafer surface and the like with high sensitivity and with high throughput.

The methods of inspecting for foreign particles and defects on the wafer are largely classified into those using a charged particle beam such as an electron beam or the like and those using light. The methods using light include one that uses a camera to take an image of the wafer surface to analyze the image information, and one that uses a light receiving element like a photomultiplier tube to detect scattered light on the wafer surface to analyze the degree of scattering of light. For example, in a surface inspection apparatus of the type irradiating the surface of the wafer with a laser beam, the scattered light from foreign particles caused by irradiation with the laser beam is detected by a detector and is subjected to analog-to-digital conversion to be output as coordinate data. To increase the throughput of inspection, an inspection table with a work (wafer) mounted thereon is rotated at high speed, and a stage mounted with the inspection table is scanned horizontally in an axial direction. As a surface inspection apparatus of this type, one described in JP-A-55-102233, for example, is known.

SUMMARY OF THE INVENTION

In the method of irradiating a wafer surface with a laser beam and detecting scattered light from foreign particles or defects, detection sensitivity would be improved if the density of energy of laser irradiation is increased. However, it has become found that when the foreign particles are made of organic matter prone to break down, the foreign particles may be broken down (destructed) by heat of the laser irradiation, in which case the particles broken down would fly around the area and adhere to the wafer surface to thereby contaminate the wafer. Conventional inspection apparatuses use laser of low power, and thus, such phenomenon of destruction of foreign particles by the laser beam did not occur. However, with an increase in sensitivity of detection of foreign particles, laser of high power has come to be used, and thus, the phenomenon of destruction of foreign particles by laser irradiation has begun to emerge. Further, in the wafer surface inspection apparatus, inspection is carried out while rotating the work (wafer) to be measured, as described above. Thus, the destructed particles would fly around the area and adhere to the wafer surface in a spiral fashion over a wide area, to contaminate the wafer.

For a wafer surface inspection apparatus, high cleanliness and high precision coordinate repeatability of foreign particles are required. The wafer contamination attributable to the destruction of foreign particles, however, would degrade such performance. To address this problem, although the density of energy of laser irradiation may be decreased to avoid destruction of foreign particles, it would lower detection sensitivity as well. Accordingly, there is a demand for a method that can prevent destruction of foreign particles attributable to laser without lowering the detection sensitivity.

An object of the present invention is to provide a wafer surface inspection apparatus that is highly sensitive and free of degradation of device performance in terms of cleanliness, coordinate repeatability of foreign particles and the like.

It is considered that foreign particles are broken down (destructed) by irradiation with a laser beam because the temperature of the particles increases due to the irradiation with the laser beam. Thus, by spraying gas for cooling onto the laser irradiation position on the wafer, the increase in temperature of the foreign particles can be prevented to suppress destruction of the foreign particles. The conditions for spraying gas for cooling depend on the density of energy at the point of laser irradiation. That is, when the density of energy is large, it is necessary to increase the flow velocity and the flow rate of the gas for cooling to increase the amount of heat radiation from the foreign particles.

JP-A-55-102233 describes that upon detection of foreign particles on the wafer, air is blown to blow off the particles. However, the foreign particles generally adhere to the wafer so firmly that they would not be blown off by just blowing the air. Rather, blowing off the foreign particles would pose another problem that the range of contamination would increase. In the present invention, gas of high cleanliness enough to cool the foreign particles is sprayed at the flow velocity and the flow rate with which the foreign particles would not be blown off. Further, in JP-A-55-102233, the air is blown before analysis, i.e., before irradiation of light, to blow off the foreign particles. In contrast, in the present invention, the gas for cooling is sprayed onto the laser irradiation position at the same time as irradiation of the laser beam, in order to cool the foreign particles being irradiated with the laser beam.

Namely, the wafer surface inspection apparatus according to an aspect of the present invention includes: a table holding a semiconductor wafer; light irradiation means for irradiating a small area on a surface of the semiconductor wafer held on the table with a laser beam; light detection means for detecting light scattered from the semiconductor wafer by irradiation with the laser beam; table drive means for rotating and concurrently linearly moving the table with respect to the light irradiation means; and gas spraying means for spraying gas onto the area on the semiconductor wafer irradiated with the laser beam by the light irradiation means. Preferably, the apparatus has a control unit controlling the light irradiation means and the gas spraying means, and the light irradiation means and the gas spraying means are controlled by the control unit such that the gas is sprayed from the gas spraying means at least while the beam is irradiated from the light irradiation means.

According to the present invention, irradiation of laser and spraying of gas with respect to the wafer are carried out at the same time and for the same location. This can increase the density of energy of irradiated laser at the limit of not destroying the foreign particles, compared to the conventional case.

Accordingly, it is possible to carry out the inspection without destructing the foreign particles, while preventing lowering of detection sensitivity.

Other objects, features and advantages of the present invention will become apparent from the following description of the embodiments of the present invention when taken with the accompanying drawings.

DESCRIPTION OF THE EMBODIMENTS

The inspection method and the inspection apparatus of the present invention are applicable to a flat plate-shaped subject to be inspected, such as a semiconductor wafer, a glass substrate for a liquid crystal panel, a disk substrate and the like. In the following, embodiments of the present invention will be described with reference to the drawings, taking a semiconductor wafer as an example.

Figure 1:
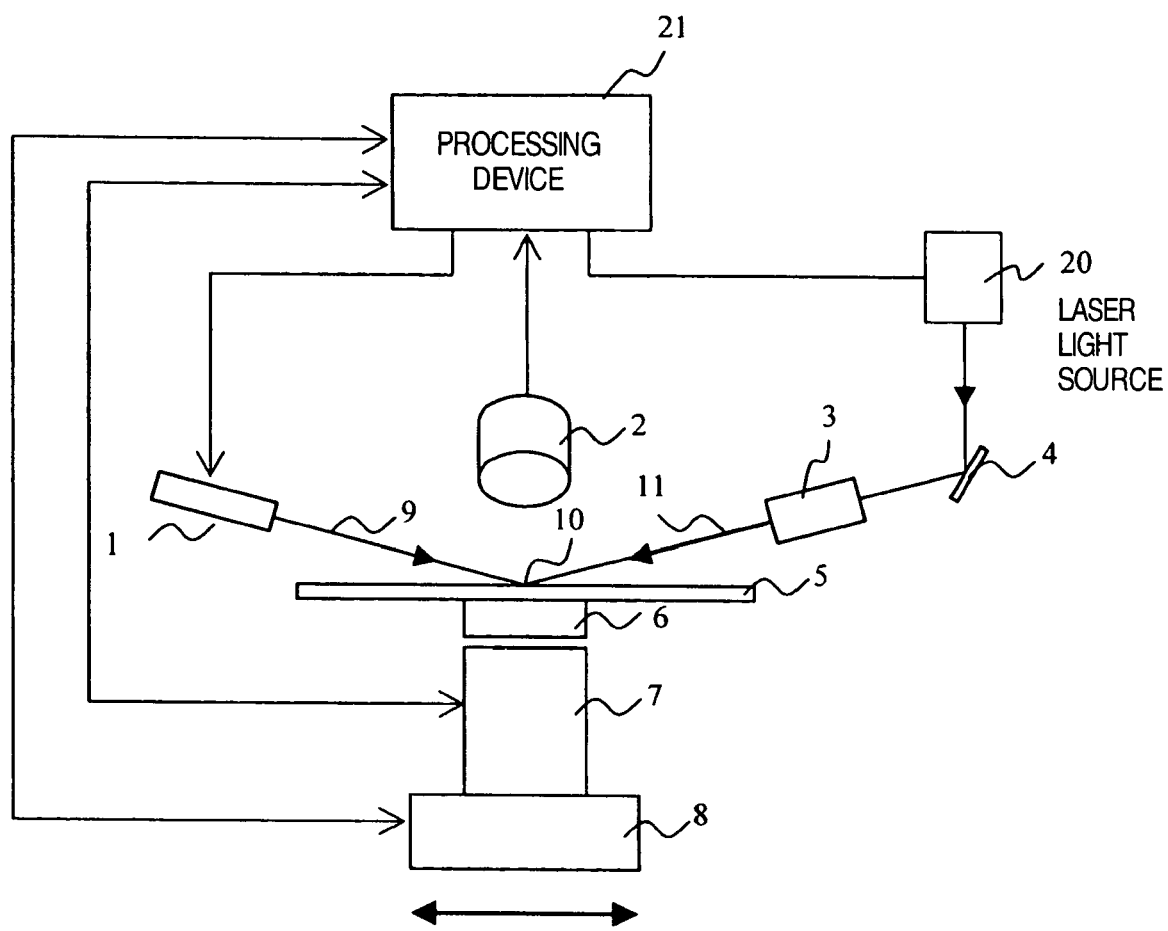
FIG. 1 is a diagram showing a schematic configuration of a wafer surface inspection apparatus according to the present invention.

FIG. 1 shows a schematic configuration of a foreign particle inspection apparatus of the present invention incorporating gas spraying means (gas spraying unit).

A semiconductor wafer 5 that is the subject to be inspected is rested on an inspection table 6, serving also as holding means (holder) or vacuum suction means (vacuum suction device), and is clamped or held with vacuum. A scanning stage 8 is mounted with an air spindle motor 7 to which inspection table 6 is attached, and is capable of generally horizontal movement backwards and forthwards in an axial direction. Air spindle motor 7 rotates at high speed in the θ direction while controlling inspection table 6 to a prescribed speed, and at the same time, the scanning stage 8 moves inspection table 6 in the scanning direction. A detection system 2 and a laser irradiation position 10 are stationary. Semiconductor wafer 5 relatively moves with respect to laser irradiation position 10, so that the area of laser irradiation position 10 is cooled by fixedly providing the gas spraying means at an arbitrary position. The gas spraying means is constructed by eliminating sliding parts to the greatest possible extent, to restrict generation of dust from the gas spraying means.

A laser beam 11 irradiated from a laser light source 20 is reflected by a mirror 4 to pass through a projecting portion 3, and is then directed to laser irradiation position 10 on the surface of semiconductor wafer 5. With laser irradiation position 10 being fixed, semiconductor wafer 5 is moved relatively in the scanning direction while being rotated at high speed in the θ direction, to detect foreign particles on the entire surface of semiconductor wafer 5. As laser irradiation position 10 is irradiated with laser beam 11, scattered light is generated from foreign particles or defects, which scattered light is detected by detection system 2. Gas 9 of high cleanliness is sprayed onto laser irradiation position 10 of semiconductor wafer 5 from gas spraying unit 1 continuously at least during the time in which laser beam 11 is irradiated.

In the example shown in FIG. 1, the gas spraying direction from gas spraying unit 1 to laser irradiation position 10 is opposite to the irradiation direction of the laser beam. The gas spraying direction does not affect cooling efficiency of the area of laser irradiation position 10, and similar effects can be obtained when it is set to any direction with respect to the laser irradiation direction. As the gas for cooling, dry air or nitrogen gas, or gas exhibiting high thermal conductivity, such as helium, argon or the like, may be used.

Laser light source 20 and gas spraying unit 1 are controlled by a CPU or processing device 21. The output of detection system 2 is subjected to analog-to-digital conversion, and is input to CPU or processing device 21. Rotation angle data of air spindle motor 7 and position data of scanning stage 8 are also input to CPU or processing device 21. When the output of detection system 2 exceeds a predetermined threshold value, CPU or processing device 21 obtains the coordinate on the wafer from the rotation angle data of air spindle motor 7 and the position data of scanning stage 8, and stores the same as defect coordinate data.

Figure 2:
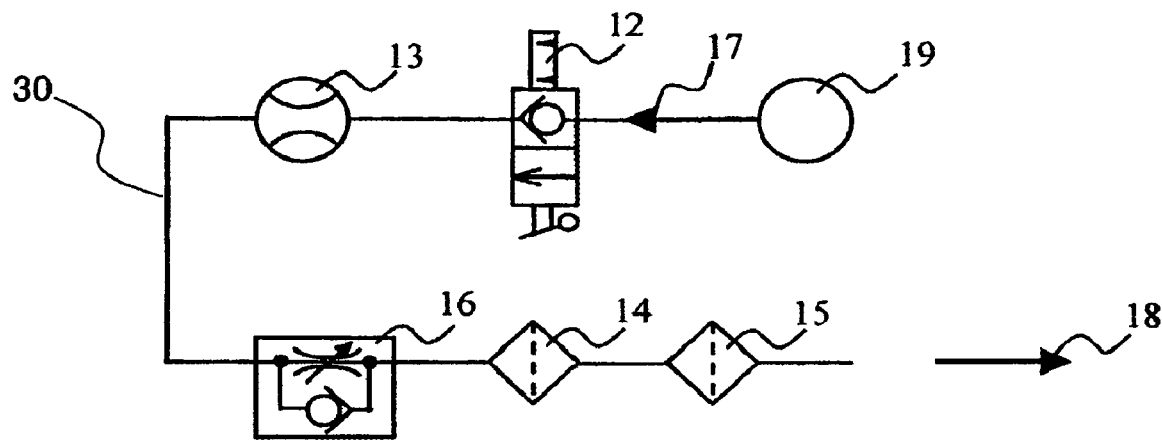
FIG. 2 is a configuration diagram (piping system diagram) of an air blow unit.

FIG. 2 is a schematic diagram showing an air circuit of the gas spraying unit 1. The air circuit includes pressurizing means (pressurizing device) of gas 17, made of a compressor 19 or the like, dehumidifier means (dehumidifier device) made of an air dryer (not shown) or the like, supply path open/close means (supply path open/close device) made of an air valve 12 or the like, flow rate measuring means (flow meter) made of a purge meter 13, MFM (mass flow meter) or the like, flow rate variable means (flow rate variable device) made of a speed controller 16, needle valve or the like, dust control means (dust control device) arranged in a plurality of stages, made of two or more filters or the like, and a supply pipe 30 for connecting these elements. The overall supply of gas 17 is controlled via CPU or processing device 21.

The pressurizing means and the dehumidifier means in the configuration may be substituted with dry air supplied as the plant utilities on the semiconductor manufacturing line, or may be provided individually for the inspection apparatuses. In either case, similar effects can be obtained. In order to use a gas type different from the air or to suppress disturbance from the plant side, it is preferable to mount them individually to the inspection apparatuses. When placing greater importance on downsizing and manufacturing cost of the inspection apparatuses, it is preferable to substitute them with the dry air.

Figure 5:
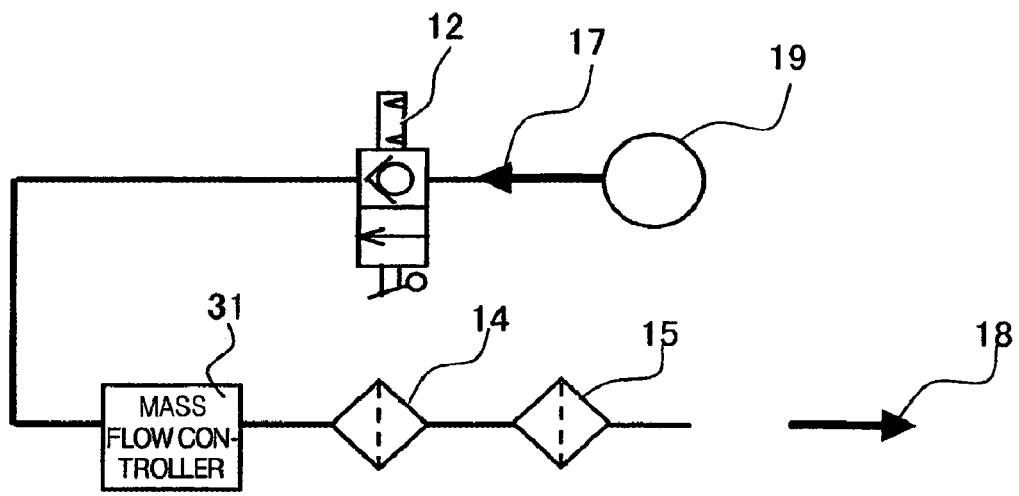
FIG. 5 is a diagram (piping system diagram) showing an air blow unit incorporating a mass flow controller.

As shown in the figure, gas 17 increased to a prescribed pressure by compressor 19 is controlled to a prescribed dew point by the air dryer, and is supplied through supply pipe 30. Inflow gas 17, of which supply and shut-off is controlled by valve 12, passes through purge meter 13 that measures a flow rate of gas 17. Thereafter, gas 17 is adjusted by speed controller 16 to the flow rate that would not contaminate the wafer. After passing through a first filter 14 (first dust control means) and a second filter 15 (second dust control means), the gas is sprayed onto the surface of semiconductor wafer 5 as sprayed gas 18. Foreign particles (dust) within gas 17 are removed (captured) by first filter 14 (first dust control means) and second filter 15 (second dust control means) provided in a plurality of stages, and thus, sprayed gas 18 is sprayed as the gas of high cleanliness. It is noted that speed controller 16 and purge meter 13 may be configured with flow rate control means (flow rate control device) such as a MFC 31 (mass flow controller) or the like, serving as both the flow rate measuring means and the flow rate variable means, as shown in FIG. 5. This allows gas 17 to be supplied at a stable flow rate with accuracy, without being affected by variation in pressure of compressor 19. Accordingly, the cooing performance by sprayed gas 18 is stabilized, and thermal destruction of foreign particles can be suppressed effectively, and thus, coordinate repeatability of the foreign particles improves.

The set value of the flow rate of gas 17, controlled by MFC 31, is set in a freely changeable manner via a setting screen provided on display means (not shown) formed with a CRT or flat panel display, using input means (input unit) 5 (not shown) formed with a keyboard, touch panel, mouse or the like. The input set value is registered to CPU or processing device 21. CPU or processing device 21, based on the flow rate set value, controls via MFC 31 such that the prescribed flow rate of gas 17 is maintained in a stable manner.

Figure 6:
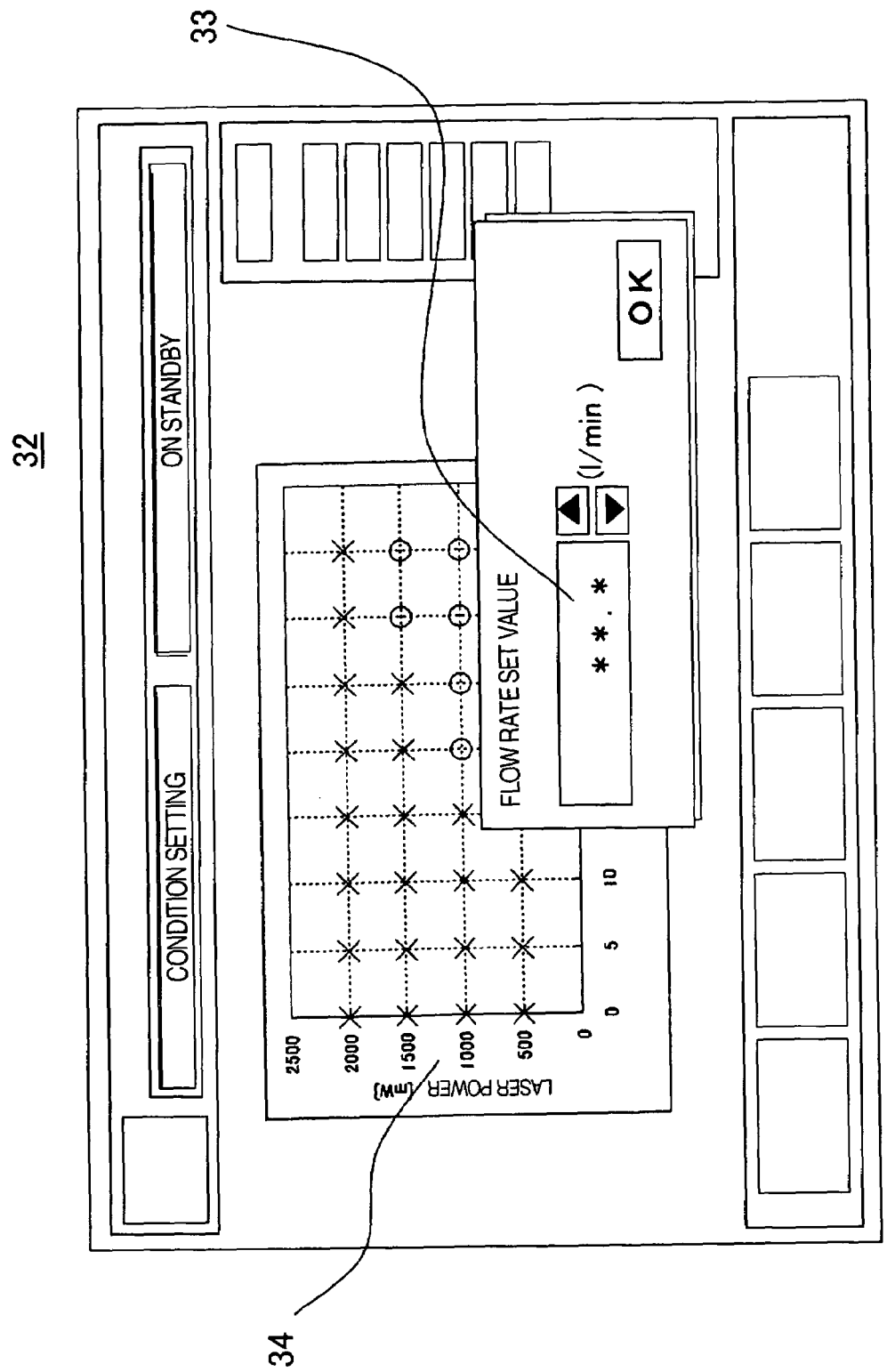
FIG. 6 shows a setting screen of gas flow rate and a displayed state of scatter plot.

FIG. 6 shows a flow rate setting screen of the present embodiment. It is configured such that the set value of flow rate supplied from gas spraying unit 1 can be input, via an input device 520, to a flow rate set value input space 33 that is displayed on the setting screen 32 provided on the display means (display device). The flow rate of gas 17 is controlled in the above-described manner, based on the set value.

Although the flow rate of gas 17 is set via input space 33 in the present embodiment, not limited to input space 33, it may be set via another screen opened with an icon or button provided on the setting screen. Any screen enabling setting of at least the set value of flow rate of gas 17 may be used.

Figure 3A:
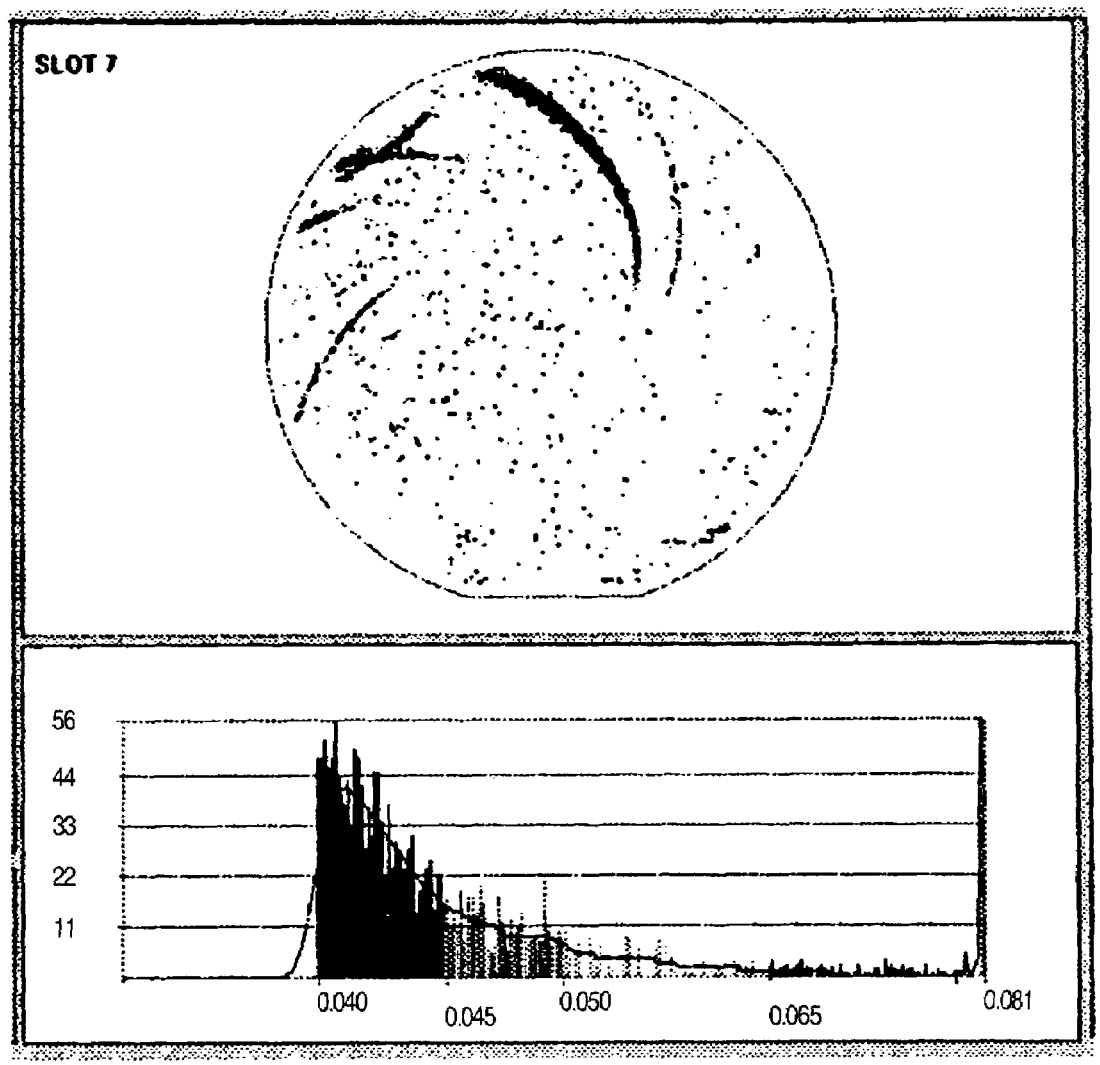
FIG. 3A shows that contamination in a spiral form has occurred with a conventional inspection method.
Figure 3B:
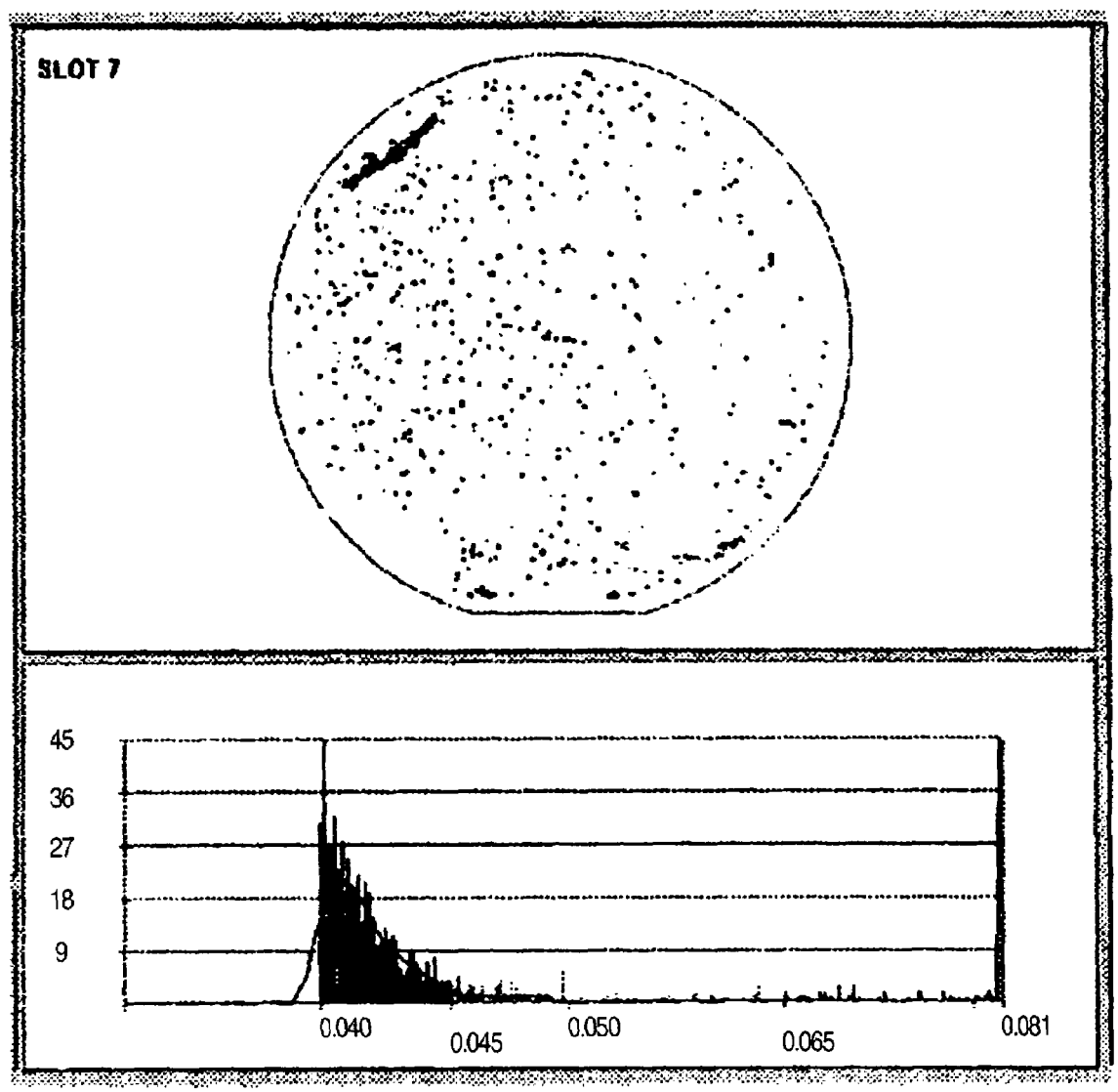
FIG. 3B shows a result of inspection by a method of the present invention.

FIGS. 3A and 3B show the effect of suppressing thermal destruction of foreign particles by the gas spraying means.

FIG. 3A shows a map (distribution of foreign particles) of the wafer in the state of occurrence of contamination in a spiral fashion (detection sensitivity: 40 nm or more). It shows that, with the inspection carried out by a conventional method without spraying of gas, foreign particles adherent to the wafer are destroyed by laser irradiation and scattered around the area, which adhere to the wafer in the shape of bands. The foreign particles are distributed in a spiral manner from the inner side toward the outer side, because the inspection was carried out while rotating the wafer, causing the scattered foreign particles to move outward along the flow of the air that occurs from the inner side toward the outer side on the wafer surface during inspection due to viscosity of the air.

FIG. 3B shows a map of the wafer in the state of absence of spiral contamination (detection sensitivity: 40 nm or more). The inspection was conducted under the conditions exactly the same as in FIG. 3A, except that the gas was sprayed onto the laser irradiation area on the wafer.

Spiral contamination as in FIG. 3A has not occurred, showing a significant effect of suppressing thermal destruction of foreign particles by the gas spraying means. It is noted that the inspection was carried out in the following order: (1) perform inspection of the initial state, (2) cause foreign particles to adhere, (3) conduct measurement of FIG. 3B, and (4) conduct measurement of FIG. 3A. That is, FIGS. 3A and 3B are diagrams confirming that the foreign particles are destroyed in the absence of gas spraying, after confirming presence of the gas spraying effect.

Figure 4:
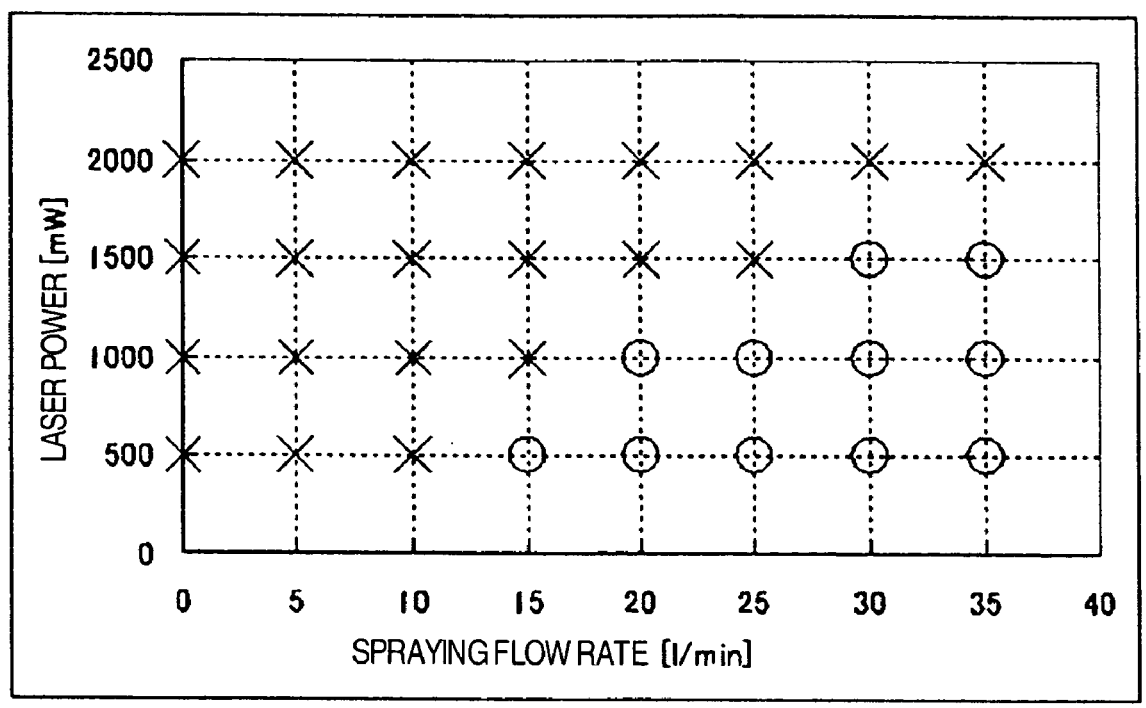
FIG. 4 shows the relation between the laser power and the gas spraying flow rate having an effect of suppressing destruction of foreign particles.

FIG. 4 shows the relation between the laser power and the flow rate of sprayed gas having the effect of suppressing destruction of foreign particles, obtained through experiments.

The experimental conditions are as follows:
(1) laser wavelength: 532 nm
(2) laser spot diameter: elliptical shape of 50 μm×10 μm
(3) spindle rotational speed: 1500 r/min
(4) stage feed pitch: 20 μm
(5) foreign particle detection sensitivity: 40 nm
(6) inner diameter of gas (air) spraying nozzle: 2.5 mm
(7) evaluated wafer: bare wafer of φ 300 mm
(8) air spraying angle (elevation angle): 23°

The experimental methodology is as follows:
(1) Perform measurement of the wafer in the initial state.
(2) Intentionally cause foreign particles that would readily be destroyed (e.g., organic matter) to adhere to the wafer surface.
(3) Perform measurement in the state where air is sprayed onto the portion irradiated with laser.
(4) Perform measurement in the state where air is not sprayed onto the portion irradiated with laser.
(5) Determine that there is the air spraying effect and mark "O" when spiral contamination does not occur in (3) but occurs in (4).
(6) Determine that there is no air spraying effect and mark "X" when spiral contamination occurs in (3).
(7) Determine that adherence of foreign particles is insufficient when no spiral contamination occurs in both (3) and (4), and cause the foreign particles to adhere again and perform measurement of (3) and (4).
(8) Conduct evaluation of (2) through (7) using the air spraying flow rate [l/min] and the laser power [mW] as parameters.

The method for determining the air spraying effect is as follows. The state after measurement is compared with the initial state before adherence of the foreign particles. It is determined that there is no air spraying effect if there is spiral contamination as shown in FIG. 3A or the track of destruction of the foreign particles. In contrast, it is determined that there is the air spraying effect if there is no spiral contamination compared with the initial state.

It has been confirmed that the spraying of the air has an effect of reducing the range of contamination even in the area shown by X where the foreign particles are destroyed. This is presumably because the flow of the air on the wafer surface during inspection is disturbed by the sprayed air, making it difficult for them to adhere to the wafer.

It is understood from the result of FIG. 4 that the gas spraying flow rate required to suppress destruction of foreign particles increases as the laser power increases, and that the flow rate of at least 15 l/min or more is required with the laser power of 500 mW or more that is necessary for detection of fine foreign particles. It however has been confirmed that the gas supplied with the flow rate exceeding 30 l/min would likely blow off the adhered foreign particles. As such, it is desirable that the flow rate of gas 17 is set preferably in the range of 15 to 30 l/min to guarantee the performance of foreign particle repeatability. More desirably, using the following expression 1 obtained from the result of FIG. 4, the flow rate is set preferably in the range of not lower than the flow rate obtained from the expression 1 and not greater than 30 l/min:

$$y=0.015x+7.5 \quad \text{(expression 1)}$$

where y is the spraying flow rate of gas 17 (l/min), and x is the laser power (mW). When gas of high thermal conductivity, such as helium gas or the like, is used, a greater effect of suppressing thermal destruction can be obtained with the less flow rate of gas 17, which can improve both the detection sensitivity and the foreign particle repeatability.

Further, the relation between the laser power and the spraying flow rate shown in FIG. 4 is displayed as a scatter plot 34 on the setting screen provided on the display means shown in FIG. 6 or on a screen of database separately provided. By displaying scatter plot 34 as the reference data, it is possible to prevent a setting error of flow rate of gas 17 with respect to the laser power. Furthermore, it is configured to allow an alarm message to be displayed on the display means or the registration to be rejected, when the flow rate setting of gas 17 out of the relation of FIG. 4 with respect to the laser power is input, based on the expression 1 above and the upper limit of the flow rate.

As described above, according to the present embodiment, gas of high cleanliness is sprayed, which ensures that inspection of the wafer is carried out while maintaining the conventional cleanliness. The adhered foreign particles are not blown off, which ensures that the conventional performance of foreign particle repeatability is maintained. Further, according to the present embodiment, it is possible to increase the density of laser energy at the limit of not destroying the foreign particles. Even in the event that the laser beam is irradiated exceeding the laser energy density at the limit of not destroying the foreign particles, the range of scattering of the destroyed foreign particles can be made smaller than in the conventional case.

Although the embodiments of the present invention have been described above, it will be apparent to a person skilled in the art that the present invention is not limited thereto, but various changes and modifications are possible within the sprit of the present invention and within the scope of the appended claims.

The invention claimed is:

1. A wafer surface inspection apparatus comprising:
   a table holding a semiconductor wafer;
   a light irradiation means for irradiating a small area on a surface of the semiconductor wafer held on said table with a laser beam;
   a light detection means for detecting light scattered from the semiconductor wafer by irradiation with said laser beam;
   a table drive means for rotating and concurrently linearly moving said table with respect to said light irradiation means; and
   a gas spraying means for spraying gas onto the small area on the surface of the semiconductor wafer irradiated with the laser beam by said light irradiation means, so as to cool the small area on the surface of the semiconductor wafer.

2. The wafer surface inspection apparatus according to claim 1, having a control unit for controlling said light irradiation means and said gas spraying means, wherein said control unit is configured to control said light irradiation means and said gas spraying means such that the gas is sprayed from said gas spraying means at least while the beam is irradiated from said light irradiation means.

3. A wafer surface inspection apparatus according to claim 1, wherein said gas spraying means is configured to spray gas at a volumetric rate of at least 15 liters per minute, and less than 30 liters per minutes.

4. A wafer surface inspection apparatus according to claim 3, wherein said gas spraying means is configured to spray gas at a volumetric flow rate of approximately y liters/minute, wherein $y=0.15x+7.5$, and wherein x is a laser power in milliwatts.

5. A waver surface inspection apparatus according to claim 1, wherein said gas spraying means is configured to spray a gas with high thermal conductivity.

6. A wafer surface inspection method for inspecting a surface of a semiconductor wafer, comprising the steps of:
   irradiating a small area on a surface of a rotating semiconductor wafer with a laser beam;
   spraying a cooling gas onto the small area on the surface of the rotating semiconductor wafer irradiated with the laser beam at least while the small area on the surface of the rotating semiconductor wafer is irradiated with the laser beam;
   detecting scattered radiation from the small area; and
   outputting, displaying, storing for later use, or using information about the detected scattered radiation.

* * * * *